(12) United States Patent
Fu et al.

(10) Patent No.: US 10,071,973 B2
(45) Date of Patent: Sep. 11, 2018

(54) CRYSTALLINE ISOXAZOLE HYDROXAMIC ACID COMPOUNDS

(71) Applicant: Novartis AG, Basel (CH)

(72) Inventors: Jiping Fu, Danville, CA (US); Siyi Jiang, Shanghai (CN); Andreas Kordikowski, Basel (CH); Zachary Kevin Sweeney, Redwood City, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/620,373

(22) Filed: Jun. 12, 2017

(65) Prior Publication Data

US 2017/0355684 A1    Dec. 14, 2017

(30) Foreign Application Priority Data

Jun. 14, 2016    (WO) ................ PCT/CN2016/085694

(51) Int. Cl.
| | |
|---|---|
| *C07D 261/08* | (2006.01) |
| *A61K 31/7048* | (2006.01) |
| *A61K 38/14* | (2006.01) |
| *A61K 38/12* | (2006.01) |
| *A61K 31/431* | (2006.01) |
| *A61K 31/65* | (2006.01) |
| *A61K 31/7036* | (2006.01) |
| *A61K 31/496* | (2006.01) |
| *A61K 31/5383* | (2006.01) |
| *A61K 31/42* | (2006.01) |
| *A61K 31/43* | (2006.01) |
| *A61K 31/546* | (2006.01) |

(52) U.S. Cl.
CPC ............ *C07D 261/08* (2013.01); *A61K 31/42* (2013.01); *A61K 31/43* (2013.01); *A61K 31/431* (2013.01); *A61K 31/496* (2013.01); *A61K 31/5383* (2013.01); *A61K 31/546* (2013.01); *A61K 31/65* (2013.01); *A61K 31/7036* (2013.01); *A61K 31/7048* (2013.01); *A61K 38/12* (2013.01); *A61K 38/14* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 6,111,090 A | 8/2000 | Gorman | |
| 7,025,962 B1 | 4/2006 | Gorman | |
| 7,618,632 B2 | 11/2009 | Collins | |
| 7,812,135 B2 | 10/2010 | Smith | |
| 7,943,743 B2 | 5/2011 | Korman | |
| 8,354,509 B2 | 1/2013 | Carven | |
| 8,388,967 B2 | 3/2013 | Smith | |
| 8,586,023 B2 | 11/2013 | Shiku | |
| 8,591,886 B2 | 11/2013 | Ponath | |
| 8,609,089 B2 | 12/2013 | Langermann | |
| 8,748,466 B2 | 6/2014 | Abramite | |
| 8,809,333 B2 | 8/2014 | Brown | |
| 9,549,916 B2 * | 1/2017 | Fu | ........................ A61K 31/42 |
| 9,637,482 B2 | 5/2017 | Fu | |
| 9,718,792 B2 | 8/2017 | Fu | |
| 2010/0028330 A1 | 2/2010 | Collins | |
| 2011/0150892 A1 | 6/2011 | Thudium | |
| 2012/0039906 A1 | 2/2012 | Olive | |
| 2012/0114649 A1 | 5/2012 | Langermann | |

FOREIGN PATENT DOCUMENTS

| | | |
|---|---|---|
| EP | 418667 | 8/1995 |
| EP | 090505 B1 | 8/2010 |
| EP | 1866339 | 5/2013 |
| EP | 1947183 B1 | 7/2013 |
| WO | WO 1999/20758 | 4/1999 |
| WO | WO 1999/40196 | 8/1999 |
| WO | WO 2001/03720 | 1/2001 |
| WO | WO 2004/043349 | 5/2004 |
| WO | WO 2004/062601 | 7/2004 |
| WO | WO 2005/007190 | 1/2005 |
| WO | WO 2005/055808 | 6/2005 |
| WO | WO 2005/115451 | 12/2005 |
| WO | WO 2006/082404 | 8/2006 |
| WO | WO 2006/083289 | 8/2006 |
| WO | WO 2007/005874 | 1/2007 |
| WO | WO 2009/101611 | 8/2009 |
| WO | WO 2009/114335 | 9/2009 |
| WO | WO 2010/003118 | 1/2010 |
| WO | WO 2010/019570 | 2/2010 |
| WO | WO 2010/027827 | 3/2010 |

(Continued)

OTHER PUBLICATIONS

Bennett et al., "Program Death-1 Engagement Upon TCR Activation Has Distinct Effects on Costimulation and Cytokine-Driven Proliferation: Attenuation of ICOS, IL-4, and IL-21, But Not CD28, IL-7, and 1L-15 Responses" J. Immunol. 170:711-718, 2003.

(Continued)

*Primary Examiner* — Kamal Saeed
(74) *Attorney, Agent, or Firm* — Mark H. Hopkins

(57) ABSTRACT

This invention pertains to a crystalline compound of Formula (A) as described herein and compositions containing this crystalline compound, as well as methods of using the compound or pharmaceutical compositions comprising it to treat bacterial infections. The compound and compositions are especially useful to treat Gram negative bacterial infections, including multi-drug resistant strains.

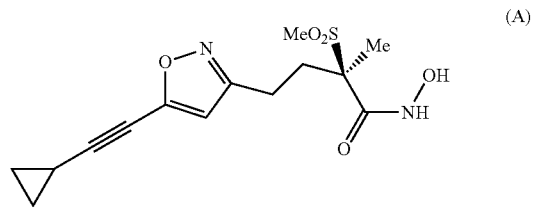

(A)

15 Claims, 4 Drawing Sheets

(56) References Cited

FOREIGN PATENT DOCUMENTS

| WO | WO 2010/032147 | 3/2010 |
|----|----------------|--------|
| WO | WO 2010/077634 | 7/2010 |
| WO | WO 2011/028683 | 3/2011 |
| WO | WO 2011/045703 | 4/2011 |
| WO | WO 2011/051726 | 5/2011 |
| WO | WO 2011/066342 | 6/2011 |
| WO | WO 2011/073845 | 6/2011 |
| WO | WO 2011/090754 | 7/2011 |
| WO | WO 2007/133822 | 11/2011 |
| WO | WO 2012/032014 | 3/2012 |
| WO | WO 2012/120397 | 9/2012 |
| WO | WO 2012/137094 | 10/2012 |
| WO | WO 2012/137099 | 10/2012 |
| WO | WO 2012/154204 | 11/2012 |
| WO | WO 2013/039954 | 3/2013 |
| WO | WO 2013/079174 | 6/2013 |
| WO | WO 2014/008218 | 1/2014 |
| WO | WO 2014/160649 | 10/2014 |
| WO | WO 2015/164458 | 10/2015 |
| WO | WO 2016/097995 | 6/2016 |

OTHER PUBLICATIONS

Blank et al., "Interaction of PD-L1 on tumor cells with PD-1 on tumor-specific T cells as a mechanism of immune evasion: implications for tumor immunotherapy" Cancer Immunol. Immunother. 54(4):307-314, 2005.

Blank, C. et al., "Contribution of the PD-L1/PD-1 pathway to T-cell exhaustion: an update on implications for chronic infections and tumor evasion" Immunol. Immunother. 56(5):739-745, (Epub Dec. 29, 2006).

Brown et al.,"Blockade of Programmed Death-1 Ligands on Dendritic Cells Enhances T Cell Activation and Cytokine Production" J. Immunol. 170:1257-1266, 2003.

Dong et al. "B7-H1 pathway and its role in the evasion of tumor immunity" J. Mol. Med. 81(5):281-287, 2003.

Hamid, O. et al., "Safety and Tumor Responses with Lambrolizumab (Anti-PD-1) in Melanoma" New England Journal of Medicine 369(2):134-44, 2013.

Hyland et al., "Cloning, Expression, and Purification of UDP-3-O-Acyl-GlcNAc Deacetylase from Pseudomonas aeruginosa: a Metalloamidase of the Lipid A Biosynthesis Pathway" Journal of Bacteriology 179(6):2029-2037, 1997.

Ishida, Y. et al., "Induced expression of PD-1, a novel member of the immunoglobulin gene superfamily, upon programmed cell death" EMBO J. 11:3887-3895, 1992.

Iwai et al., "Involvement of PD-L1 on tumor cells in the escape from host immune system and tumor immunotherapy by PD-L1 blockade" Proc. Nat'l. Acad. Sci. USA 99(19):12293-12297, 2002.

Konishi et al., "B7-H1 expression on non-small cell lung cancer cells and its relationship with tumor-infiltrating lymphocytes and their PD-1 expression" Ciin. Cancer Res. 10:5094-5100, 2004.

McAllister et al., "Heterocyclic Methylsulfone Hydroxamic Acid LpxC Inhibitors as Gram-Negative Antibacterial Agents" Bioorganic & Medicinal Chemistry Letters 22:6832-6838, 2012.

Mdluli, et al., "Molecular validation of LpxC as an antibacterial drug target in Pseudomonas aeruginosa" Antimicrobial Agents and Chemotherapy, 50(6):2178-2184, 2006.

Okazaki et al., "New regulatory co-receptors: inducible co-stimulator and PD-1" Curr Opin Immunol 14:391779-82, 2002.

Piizzi, "Design, Synthesis and Properties of Potent Inhibitors of Pseudomonas aeruginosa Deacetylase LpxC" Global Discovery Chemistry Novartis AG, Switzerland EFMC Meeting, Lisbon, Sep. 9, 2014.

* cited by examiner

CRYSTALLINE ISOXAZOLE HYDROXAMIC ACID COMPOUNDS

CROSS-REFERENCE TO RELATED APPLICATION

This application claims the benefit of priority to international Application No. PCT/CN2016/085694, filed Jun. 14, 2016, the contents of which are incorporated herein by reference.

FIELD OF THE INVENTION

This invention pertains generally to compounds and compositions and methods for treating bacterial infections. In certain aspects, the invention pertains to a crystalline form of a hydroxamic acid compound, Compound (A), that is useful for treating infections caused by Gram-negative bacteria, and pharmaceutical compositions comprising the crystalline compound described herein. In one aspect, the invention pertains to treating Gram-negative infections using the crystalline compound disclosed herein.

BACKGROUND

Over the past several decades, the frequency of antimicrobial resistance and its association with serious infectious diseases have increased at alarming rates. The increasing prevalence of pathogens resistant to one or more of the approved antibiotics for treating infectious agents causing nosocomial infections, also called hospital-acquired infections, is particularly disconcerting. Of the over 2 million nosocomial infections occurring each year in the United States, 50 to 60% are caused by antimicrobial-resistant strains of bacteria. The high rate of resistance to commonly-used antibacterial agents increases the morbidity, mortality, and costs associated with nosocomial infections. In the United States, nosocomial infections are thought to contribute to or cause more than 77,000 deaths per year and cost approximately $5 to $10 billion annually. Only a few classes of approved antibacterials are effective on Gram-negative bacteria, and many of the approved drugs are losing effectiveness as resistant strains of Gram negative bacteria become more prevalent. Important causes of Gram-negative resistance include extended-spectrum β-lactamases (ESBLs) in *Klebsiella pneumoniae*, *Escherichia coli*, and *Proteus mirabilis*, high-level third-generation cephalosporin (Amp C) β-lactamase resistance among *Enterobacter* species and *Citrobacter freundii*, and multidrug-resistance (MDR) genes observed in *Pseudomonas* species, *Acinetobacter* species, and *Stenotrophomonas* species.

The problem of antibacterial resistance is compounded by the existence of bacterial strains resistant to multiple families of antibacterials. For example, *Pseudomonas aeruginosa* isolates resistant to fluoroquinolones are virtually all resistant to additional antibacterial medicines as well. Much of the antibacterial discovery effort in the pharmaceutical industry is aimed at the development of drugs effective against Gram-positive bacteria. However, there is an urgent need for new Gram-negative antibacterials, which are in general more resistant to most antibacterials than are Gram-positive bacteria. Such antibacterial compounds acting on lipopolysaccharide biosynthesis have been reported, including various hydroxamic acid compounds: see for example WO2004/062601, WO2010/032147, WO2011/073845, WO2012/120397, and WO2012/137094. One lipopolysaccharide biosynthesis enzyme, UDP-3-O—(R-3-hydroxydecanoyl)-N-acetylglucosamine deacetylase (LpxC), has been reported as a validated target for antibacterials. (Mdluli, et al., *Antimicrobial Agents and Chemotherapy*, 50(6), 2178-84 (2006).) While inhibitors of LpxC have been described, there remains a need for new LpxC inhibitors with better antibacterial efficacy, especially on MDR strains. The current invention provides a crystalline compound that is believed to act by inhibition of LpxC and that avoid some of the prevalent mechanisms of resistance to known antibacterial agents, and is especially suitable for use in the manufacture of antibacterial products on commercial scale.

BRIEF SUMMARY

In one aspect, the invention provides a novel crystalline form of this compound

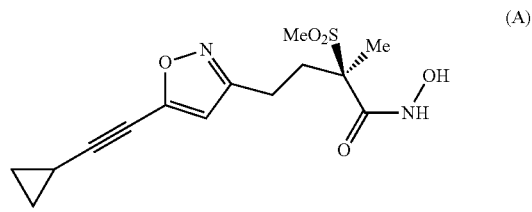 [SMILES: C[C@@](CCc1cc(C#CC2CC2)on1)(C(=O)NO)S(C)(=O)=O]

and methods of making and using this crystalline material. The crystalline material is well suited for use in commercial production processes, because it has low hygroscopicity and provides consistent processing and handling characteristics that are needed for high volume production or manufacturing. Without being bound by theory, Compound (A) is believed to act by inhibiting the activity of UDP-3-O—(R-3-hydroxydecanoyl)-N-acetylglucosamine deacetylase (LpxC). The inhibitor can be used to treat bacterial infections, especially Gram-negative infections including drug-resistant and multi-drug resistant infections, in subjects including humans, and may be used alone or in combination with other therapeutic agents such as other antibacterials.

In one aspect, the invention provides Compound (A) in crystalline form. This compound is disclosed and claimed in unpublished patent application PCT/IB2015/059631 (filed 15 Dec. 2015). The synthetic method in that application provides compound (A) in an amorphous form, which proved to be deliquescent and developed a brownish color over time when left at room temperature. Because of those properties, the amorphous material was not well suited to large scale manufacture or prolonged storage. The present invention provides a well-behaved crystalline form of Compound (A) that is more consistent and more stable, and has low hygroscopicity, and is thus especially suitable for use in automated manufacturing processes and apparatus, and for large-scale manufacturing methods needed for commercial production. The crystalline product need not be purely crystalline: it may retain some amorphous material, but is preferably mostly crystalline (e.g., more than 50% crystalline) or substantially crystalline, e.g. at least 75% crystalline. Degree of crystallinity can be assessed by methods known in the art, such as XRPD.

In another aspect, the invention provides methods of producing Compound (A) in crystalline form. One such method involves dissolving the amorphous material in a moderately polar solvent such as an ether (e.g., diethyl ether, THF, dioxane, methyl t-butyl ether, diisopropyl ether) or a halogenated solvent (e.g., dichloromethane, trichloroethylene, tetrachloroethylene, chloroform) and inducing crystallization by cooling or by addition of a hydrocarbon solvent such as hexane or hexanes, cyclohexane, heptane or heptanes, octane or octanes, or a mixture of these. Dissolution of the amorphous material may require heating, especially when hydrocarbon or less polar ether solvents are used (MTBE, diethyl ether), while it may occur more readily in a halogenated solvent. Where heating is required to induce dissolution, cooling of the solution may be sufficient to induce crystallization; where no heating is required, it is often necessary to add a hydrocarbon solvent to induce crystallization.

In a preferred method, amorphous Compound (A) is dissolved in dichloromethane, and the solution is brought into contact with a hydrocarbon solvent such as heptane (or cyclohexane, or hexanes, etc.) underconditions that promote crystallization.

Other methods that produced at least partially crystalline material include slurrying amorphous Compound (A) in heptane, hexane, or cyclohexane in the presence of some MTBE; dissolving amorphous Compound A in a hot solvent (selected from MTBE; 1:1 heptane+ethyl acetate; 2:1 heptane+ethanol; or 1:1 isopropanol+heptane; and dissolving the amorphous Compound (A) in a 'good' solvent (e.g., dichloromethane, ethyl acetate, isopropyl acetate, isopropanol, or tetrahydrofuran) and mixing the solution with a 'poor' solvent such as hexane, heptane, cyclohexane, octane, or mixture of these, using an anti-solvent or refersed anti-solvent precipitation method. Such crystallization conditions provide material that is more stable than the initially-obtained amorphous product, which is at least partially crystalline, preferably mostly or substantially crystalline, and is also more stable and provides more consistent handling characteristics. However, material crystallized from many of these systems retained some residual solvent that was difficult to remove; thus the preferred crystallization method uses dichloromethane or a similar chlorinated organic solvent to dissolve amorphous Compound (A), followed by mixing the solution with a hydrocarbon solvent.

In another aspect, the invention provides pharmaceutical compositions comprising a crystalline form of Compound (A) admixed with a pharmaceutically acceptable carrier or excipient. Optionally, the pharmaceutical composition may comprise at least two pharmaceutically acceptable carriers and/or excipients. In certain embodiments, the pharmaceutical composition is prepared for administration in the form of a unit dosage that contains a therapeutically effective amount of Compound (A) for treatment of a subject having a Gram-negative bacterial infection. Typically, the unit dosage is in a form suitable for injection, infusion, inhalation or oral delivery.

In another aspect, the invention provides a method for treating a subject having a Gram-negative bacterial infection, wherein the method comprises administering to the subject an antibacterially effective amount of Compound (A) in crystalline form, or a pharmaceutical composition comprising Compound (A) in crystalline form.

Another embodiment of the invention provides a pharmaceutical composition comprising crystalline Compound (A) and at least one pharmaceutically acceptable carrier or excipient.

Suitably, the compositions and methods may be used to treat a subject infected with a Gram-negative bacterium selected from the group consisting of *Pseudomonas aeruginosa* and other *Pseudomonas* spp., *Stenotrophomonas maltophilia, Burkholderia cepacia* and other *Burkholderia* spp., *Alcaligenes xylosoxidans, Acinetobacter* spp., *Achromobacter* spp., *Aeromonas* spp., *Enterobacter* spp., *Eschericia coli, Haemophilus* spp., *Klebsiella* spp., *Moraxella* spp., *Bacteroides* spp., *Francisella* spp., *Shigella* spp., *Proteus* spp., *Porphyromonas* spp., *Prevotella* spp., *Mannheimia haemolyiticus, Pastuerella* spp., *Providencia* spp., *Vibrio* spp., *Salmonella* spp., *Bordetella* spp., *Borrelia* spp., *Helicobacter* spp., *Legionella* spp., *Citrobacter* spp., *Cedecea* spp., *Serratia* spp., *Campylobacter* spp., *Yersinia* spp., *Fusobacterium* spp., and *Neisseria* spp. The crystalline compound and its compositions are especially suitable for treating drug-resistant and multe-drug resistant strains of Gram negative bacteria such as *Pseudomonas aeruginosa*.

The invention also provides for the use of crystalline Compound (A) for preparing medicaments and pharmaceutical formulations, for use of the crystalline compound in inhibiting LpxC, and for use of the crystalline compound as medicaments, especially for treating bacterial infections in a subject.

The present invention is also directed to methods of combination therapy for treating or preventing a Gram-negative bacterial infection in patients, using the crystalline compound of the invention or pharmaceutical compositions thereof, or kits containing this crystalline compound or pharmaceutical compositions thereof, in combination with at least one other therapeutic agent. Other aspects of the invention are discussed herein.

DETAILED DESCRIPTION

Figure 1:
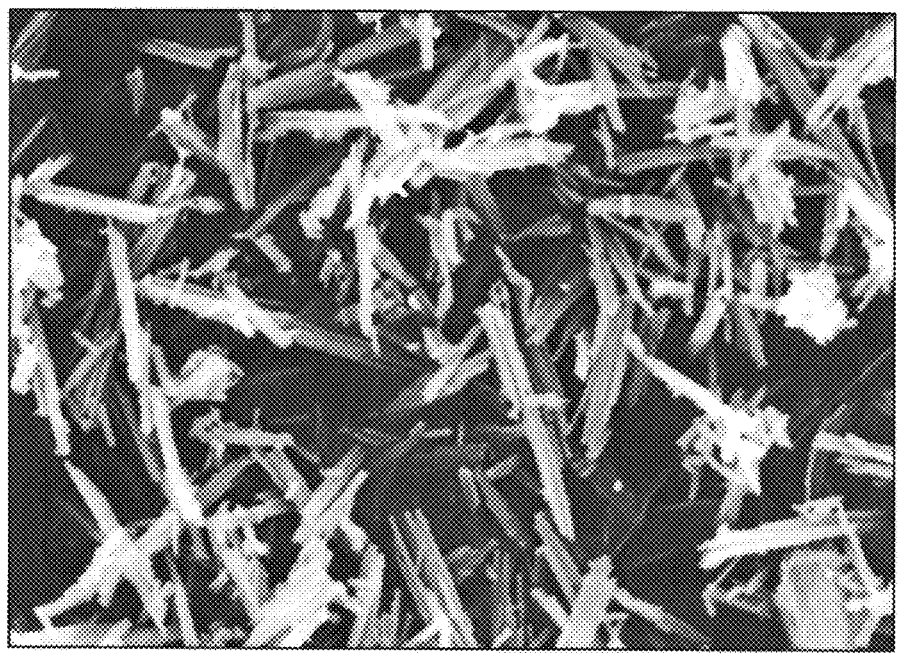
FIG. 1. SEM of Crystalline Compound A.

For purposes of interpreting this specification, the following definitions will apply, and whenever appropriate, terms used in the singular will also include the plural.

Terms used in the specification have the following meanings unless the context clearly indicates otherwise:

"LpxC" is an abbreviation that stands for UDP-3-O—(R-3-hydroxydecanoyl)-N-acetylglucosamine deacetylase. While not limited by the theory, it is believed that the compound of the invention provides its antibacterial effect primarily by inhibiting LpxC.

As used herein, the term "subject" refers to an animal. In certain aspects, the animal is a mammal. A subject also refers to for example, primates (e.g., humans), cows, sheep, goats, horses, dogs, cats, rabbits, rats, mice, fish, birds and the like. In certain embodiments, the subject is a human. A "patient" as used herein refers to a human subject.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The term "antibacterial agent" refers to agents synthesized or modified in the laboratory that have either bactericidal or bacteriostatic activity. An "active" agent in this context will inhibit the growth of *P. aeruginosa* and/or other Gram-negative bacteria. The term "inhibiting the growth" indicates that the rate of increase in the numbers of a population of a particular bacterium is reduced. Thus, the term includes situations in which the bacterial population increases but at a reduced rate, as well as situations where the growth of the population is stopped, as well as situations where the numbers of the bacteria in the population are reduced or the population is even eliminated. If an enzyme activity assay is used to screen for inhibitors, one can make modifications in bacterial uptake/efflux, solubility, half-life, etc. to compounds in order to correlate enzyme inhibition with growth inhibition.

"Halo" or "halogen", as used herein, may be fluorine, chlorine, bromine or iodine.

Various embodiments of the invention are described herein. It will be recognized that features specified in each embodiment may be combined with other specified features to provide further embodiments. The following enumerated embodiments are representative:

1. A crystalline form of the compound of Formula (A):

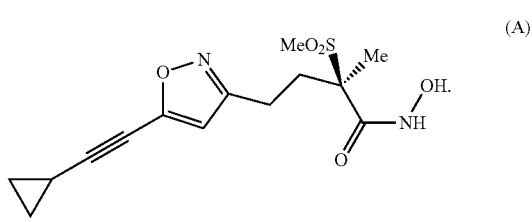 [SMILES: C[C@@](CCc1cc(C#CC2CC2)on1)(C(=O)NO)S(C)(=O)=O]

(A)

One embodiment of the invention comprises a crystalline form disclosed herein.

2. The crystalline form of embodiment 1 having low hygroscopicity. Preferably, the crystal form exhibits weight increase due to hygroscopicity of less than about 5% when a dry sample is exposed to relative humidity up to 80%; more preferably, it exhibits weight increase due to hygroscopicity of less than about 10% at relative humidity up to 90%, and typically less than 5% weight gain on exposure to relative humidity up to 90%.

3. The crystalline form of embodiment 1, which comprises rod-shaped crystals.

4. The crystalline form of embodiment 1, which exhibits an endotherm on differential scanning calorimetry between 75° C. and 90° C. Preferably, the endotherm occurs largely between 80 and 88° C., e.g. about 80% or more of the endotherm occurs in this temperature range.

5. The crystalline form of embodiment 1, characterized by XRPD peaks at diffraction angles (2Theta) of 18.4 and 14.0 degrees.

6. The crystalline form of embodiment 5, further characterized by one or more additional XRPD peaks at diffraction angles (2Theta) of 3.9 and 2.5 and 4.4 degrees.

7. The crystalline form of embodiment 5, further characterized by additional XRPD peaks at diffraction angles (2Theta) of 3.9 and 2.5 and 4.4 degrees.

8. The crystalline form of any one of embodiments 5-7, further characterized by one or more additional XRPD peaks at diffraction angles (2Theta) of 18.8 and/or 5.3 degrees and/or 21.8 degrees and/or 22.1 degrees and/or 18.0 degrees.

9. The crystalline form of any one of embodiments 5-7, further characterized by additional XRPD peaks at diffraction angles (2Theta) of 18.8 and 5.3 degrees.

10. The crystalline form of embodiment 9, further characterized by additional XRPD peaks at diffraction angles (2Theta) of 21.8 degrees and 22.1 degrees.

11. The crystalline form of embodiment 10, further characterized by an additional XRPD peak at diffraction angle (2Theta) of 18.0 degrees.

12. The crystalline form of embodiment 10, further characterized by additional XRPD peaks at diffraction angles (2Theta) of 14.3 and 13.4 degrees. This embodiment includes a crystalline form according to any of embodiments 5-11 exhibiting an XRPD spectrum substantially similar to the one in FIG. 2.

13. A pharmaceutical composition, comprising:
an antibacterially effective amount of the crystalline form of any one of embodiments 1-12; and a pharmaceutically acceptable carrier. Typically, Compound (A) in this composition consists mostly (at least 50%) of the crystalline form of one of embodiments 1-12; preferably, it consists essentially of the crystal form of one of embodiments 1-12.

14. A pharmaceutical combination, comprising:
an antibacterially effective amount of the crystalline form of any one of embodiments 1-12,
an antibacterially effective amount of a second therapeutic agent, and
a pharmaceutically acceptable carrier. Typically, Compound (A) in this combination consists mostly of a crystalline form according to one of embodiments 1-12; preferably, it consists essentially of a crystal form according to one of embodiments 1-12.

15. The pharmaceutical combination of embodiment 14, wherein the second therapeutic agent is selected from the group consisting of Ampicillin, Piperacillin, Penicillin G, Ticarcillin, Imipenem, Meropenem, Azithromycin, Erythromycin, Aztreonam, Cefepime, Cefotaxime, Ceftriaxone, Ceftazidime, Ciprofloxacin, Levofloxacin, Clindamycin, Doxycycline, Gentamycin, Amikacin, Tobramycin, Tetracycline, Tigecycline, Rifampicin, Vancomycin and Polymyxin.

16. A method of making highly crystalline form of Compound (A) from non-crystalline Compound (A), which comprises dissolving non-crystalline Compound (A) in a halogenated organic solvent to form a solution, and contacting the solution with a hydrocarbon solvent to induce precipitation of crystalline Compound (A). Preferably the non-crystalline compound (A) is amorphous, or exhibits little evidence of crystallinity on XRPD, such as less than 10% crystallinity. The highly crystalline form of Compound (A) is at least 75% crystalline, typically at least 80%, and often 90% or more crystalline, as judged by XRPD.

17. The method of embodiment 16, wherein the halogenated organic solvent is selected from dichloromethane, chloroform, ethylene dichloride, trichloroethylene, and tetrachloroethylene.

18. The method of embodiment 16 or 17, wherein the hydrocarbon solvent comprises hexane, cyclohexane, heptane, octane, or a mixture of isomers of hexane, heptane, or octane.

19. The method of embodiment 18, wherein the hydrocarbon solvent is heptane or a mixture of isomers of heptane.

20. A crystalline form of the compound of Formula (A):

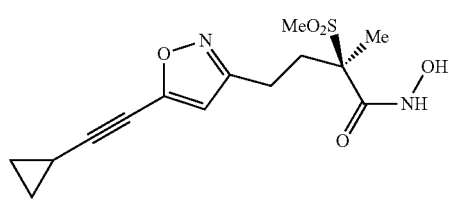

which is made by the method of embodiment 16, 17, 18 or 19. This embodiment also can be a crystalline form of Compound (A) that is obtainable by the method of embodiment 16, 17, 18 or 19. The crystalline form of this embodiment typically is characterized by descriptions set forth for any of embodiments 1-12.

21. A method for treating a subject with a Gram-negative bacterial infection, comprising:
   administering to the subject in need thereof an antibacterially effective amount of the crystalline form of any one of embodiments 1-12 or 20.

22. The method of embodiment 21, wherein the Gram negative bacterial infection is an infection comprising at least one bacterium selected from the group consisting of *Pseudomonas aeruginosa* and other *Pseudomonas* spp., *Stenotrophomonas maltophilia, Burkholderia cepacia* and other *Burkholderia* spp., *Alcaligenes xylosoxidans, Acinetobacter* spp., *Achromobacter* spp., *Aeromonas* spp., *Enterobacter* spp., *Eschericia coli, Haemophilus* spp., *Klebsiella* spp., *Moraxella* spp., *Bacteroides* spp., *Francisella* spp., *Shigella* spp., *Proteus* spp., *Porphyromonas* spp., *Prevotella* spp., *Mannheimia haemolyiticus, Pasturella* spp., *Providencia* spp., *Vibrio* spp., *Salmonella* spp., *Bordetella* spp., *Borrelia* spp., *Helicobacter* spp., *Legionella* spp., *Citrobacter* spp., *Cedecea* spp., *Serratia* spp., *Campylobacter* spp., *Yersinia* spp., *Fusobacterium* spp., and *Neisseria* spp.

23. The method of embodiment 22, wherein the bacterium is a *Pseudomonas* species and is optionally resistant to one or more antibiotics selected from piperacillin/tazobactam, imipenem, meropenem, aztreonam, cefepime, ceftazidime, methicillin, ciprofloxacin, levofloxacin, amikacin, gentamycin, and tobramycin.

24. A crystalline form of (R)-4-(5-(cyclopropylethynyl) isoxazol-3-yl)-N-hydroxy-2-methyl-2-(methylsulfonyl)butanamide obtainable by, or a crystalline form obtained by, the method of any one of embodiments 16-20, wherein the halogenated solvent is dichloromethane and the hydrocarbon solvent is heptane.

The compounds and compositions described herein can be used or administered in combination with one or more therapeutic agents that act as immunomodulators, e.g., an activator of a costimulatory molecule, or an inhibitor of an immune-inhibitory molecule, or a vaccine. The Programmed Death 1 (PD-1) protein is an inhibitory member of the extended CD28/CTLA4 family of T cell regulators (Okazaki et al. (2002) *Curr Opin Immunol* 14: 391779-82; Bennett et al. (2003) *J. Immunol.* 170:711-8). PD-1 is expressed on activated B cells, T cells, and monocytes. PD-1 is an immune-inhibitory protein that negatively regulates TCR signals (Ishida, Y. et al. (1992) *EMBO J.* 11:3887-3895; Blank, C. et al. (Epub 2006 Dec. 29) *Immunol. Immunother.* 56(5):739-745), and is up-regulated in chronic infections. The interaction between PD-1 and PD-L1 can act as an immune checkpoint, which can lead to, e.g., a decrease in infiltrating lymphocytes, a decrease in T-cell receptor mediated proliferation, and/or immune evasion by cancerous or infected cells (Dong et al. (2003) *J. Mol. Med.* 81:281-7; Blank et al. (2005) *Cancer Immunol. Immunother.* 54:307-314; Konishi et al. (2004) *Clin. Cancer Res.* 10:5094-100). Immune suppression can be reversed by inhibiting the local interaction of PD-1 with PD-L1 or PD-L2; the effect is additive when the interaction of PD-1 with PD-L2 is blocked as well (Iwai et al. (2002) *Proc. Nat'l. Acad. Sci. USA* 99:12293-7; Brown et al. (2003) *J. Immunol.* 170:1257-66). Immunomodulation can be achieved by binding to either the immune-inhibitory protein (e.g., PD-1) or to binding proteins that modulate the inhibitory protein (e.g., PD-L1, PD-L2).

In one embodiment, the combination therapies of the invention include an immunomodulator that is an inhibitor or antagonist of an inhibitory molecule of an immune checkpoint molecule. In another embodiment the immunomodulator binds to a protein that naturally inhibits the immuno-inhibitory checkpoint molecule. When used in combination with antibacterial compounds, these immunomodulators can enhance the antimicrobial response, and thus enhance efficacy relative to treatment with the antibacterial compound alone. Thus a compound of any one of embodiments 1-12 or a pharmaceutical composition of embodiment 13 can be administered to a subject who is being treated with an immunomodulator; the immunomodulator and compound can be administered together or separately, but are simultaneously used to treat an infection treatable with Compound (A) as described herein.

The term "immune checkpoints" refers to a group of molecules on the cell surface of CD4 and CD8 T cells. These molecules can effectively serve as "brakes" to down-modulate or inhibit an adaptive immune response. Immune checkpoint molecules include, but are not limited to, Programmed Death 1 (PD-1), Cytotoxic T-Lymphocyte Antigen 4 (CTLA-4), B7H1, B7H4, OX-40, CD137, CD40, and LAG3, which directly inhibit immune cells. Immunotherapeutic agents which can act as immune checkpoint inhibitors useful in the methods of the present invention, include, but are not limited to, inhibitors of PD-L1, PD-L2, CTLA4, TIM3, LAG3, VISTA, BTLA, TIGIT, LAIR1, CD160, 2B4 and/or TGFR beta. Inhibition of an inhibitory molecule can be performed by inhibition at the DNA, RNA or protein level. In some embodiments, an inhibitory nucleic acid (e.g., a dsRNA, siRNA or shRNA), can be used to inhibit expression of an inhibitory molecule. In other embodiments, the inhibitor of an inhibitory signal is a polypeptide, e.g., a soluble ligand, or an antibody or antigen-binding fragment thereof, that binds to the inhibitory molecule.

The immunomodulator can be administered concurrently with, prior to, or subsequent to, one or more compounds of the invention, and optionally one or more additional therapies or therapeutic agents. The therapeutic agents in the combination can be administered in any order. In general, each agent will be administered at a dose and/or on a time schedule determined for that agent. It will further be appreciated that the therapeutic agents utilized in this combination may be administered together in a single composition or administered separately in different compositions. In general, it is expected that each of the therapeutic agents utilized in combination be utilized at levels that do not exceed the levels at which they are utilized individually. In some embodiments, the levels utilized in combination will be lower than those utilized individually.

In certain embodiments, the antibacterial compounds described herein are administered in combination with one or more immunomodulators that are inhibitors of PD-1, PD-L1 and/or PD-L2. Each such inhibitor may be an antibody, an antigen binding fragment thereof, an immunoadhesin, a fusion protein, or an oligopeptide. Examples of such immunomodulators are known in the art.

In some embodiments, the immunomodulator is an anti-PD-1 antibody chosen from MDX-1106, Merck 3475 or CT-011.

In some embodiments, the immunomodulator is an immunoadhesin (e.g., an immunoadhesin comprising an extracellular or PD-1 binding portion of PD-LI or PD-L2 fused to a constant region (e.g., an Fc region of an immunoglobulin sequence).

In some embodiments, the immunomodulator is a PD-1 inhibitor such as AMP-224.

In some embodiments, the the immunomodulator is a PD-LI inhibitor such as anti-PD-LI antibody.

In some embodiments, the immunomodulator is an anti-PD-LI binding antagonist chosen from YW243.55.S70, MPDL3280A, MEDI-4736, MSB-0010718C, or MDX-1105. MDX-1105, also known as BMS-936559, is an anti-PD-LI antibody described in WO2007/005874. Antibody YW243.55.S70 is an anti-PD-LI described in WO 2010/077634.

In some embodiments, the immunomodulator is nivolumab (CAS Registry Number: 946414-94-4). Alternative names for nivolumab include MDX-1106, MDX-1106-04, ONO-4538, or BMS-936558. Nivolumab is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449, EP2161336 and WO2006/121168.

In some embodiments, the immunomodulator is an anti-PD-1 antibody Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) New England Journal of Medicine 369 (2): 134-44, U.S. Pat. No. 8,354,509, WO2009/114335, and WO2013/079174.

In some embodiments, the immunomodulator is Pidilizumab (CT-011; Cure Tech), a humanized IgG1k monoclonal antibody that binds to PD1. Pidilizumab and other humanized anti-PD-1 monoclonal antibodies are disclosed in WO2009/101611.

Other anti-PD1 antibodies useful as immunomodulators for use in the methods disclosed herein include AMP 514 (Amplimmune), and anti-PD1 antibodies disclosed in U.S. Pat. No. 8,609,089, US 2010028330, and/or US 20120114649. In some embodiments, the anti-PD-L1 antibody is MSB0010718C. MSB0010718C (also referred to as A09-246-2; Merck Serono) is a monoclonal antibody that binds to PD-L1.

In some embodiments, the immunomodulator is MDPL3280A (Genentech/Roche), a human Fc optimized IgG1 monoclonal antibody that binds to PD-L1. MDPL3280A and other human monoclonal antibodies to PD-L1 are disclosed in U.S. Pat. No. 7,943,743 and U.S. Publication No.: 20120039906. Other anti-PD-L1 binding agents useful as immunomodulators for methods of the invention include YW243.5.S70 (see WO2010/077634), MDX-1105 (also referred to as BMS-936559), and anti-PD-L1 binding agents disclosed in WO2007/005874.

In some embodiments, the immunomodulator is AMP-224 (B7-DCIg; Amplimmune; e.g., disclosed in WO2010/027827 and WO2011/066342), is a PD-L2 Fc fusion soluble receptor that blocks the interaction between PD1 and B7-H1.

In some embodiments, the immunomodulator is an anti-LAG-3 antibody such as BMS-986016. BMS-986016 (also referred to as BMS986016) is a monoclonal antibody that binds to LAG-3. BMS-986016 and other humanized anti-LAG-3 antibodies are disclosed in US 2011/0150892, WO2010/019570, and WO2014/008218

In certain embodiments, the combination therapies disclosed herein include a modulator of a costimulatory molecule or an inhibitory molecule, e.g., a co-inhibitory ligand or receptor.

In one embodiment, the costimulatory modulator, e.g., agonist, of a costimulatory molecule is chosen from an agonist (e.g., an agonistic antibody or antigen-binding fragment thereof, or soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In another embodiment, the combination therapies disclosed herein include an immunomodulator that is a costimulatory molecule, e.g., an agonist associated with a positive signal that includes a costimulatory domain of CD28, CD27, ICOS and/or GITR.

Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 194718361, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, the immunomodulator used is a soluble ligand (e.g., a CTLA-4-Ig), or an antibody or antibody fragment that binds to PD-L1, PD-L2 or CTLA4. For example, the anti-PD-1 antibody molecule can be administered in combination with an anti-CTLA-4 antibody, e.g., ipilimumab, for example. Exemplary anti-CTLA4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9).

In one embodiment, an anti-PD-1 antibody molecule is administered after treatment with a compound of the invention as described herein.

In another embodiment, an anti-PD-1 or PD-L1 antibody molecule is administered in combination with an anti-LAG-3 antibody or an antigen-binding fragment thereof. In another embodiment, the anti-PD-1 or PD-L1 antibody molecule is administered in combination with an anti-TIM-3 antibody or antigen-binding fragment thereof. In yet other embodiments, the anti-PD-1 or PD-L1 antibody molecule is administered in combination with an anti-LAG-3 antibody and an anti-TIM-3 antibody, or antigen-binding fragments thereof. The combination of antibodies recited herein can be administered separately, e.g., as separate antibodies, or linked, e.g., as a bispecific or trispecific antibody molecule. In one embodiment, a bispecific antibody that includes an anti-PD-1 or PD-L1 antibody molecule and an anti-TIM-3 or anti-LAG-3 antibody, or antigen-binding fragment thereof, is administered. In certain embodiments, the combination of antibodies recited herein is used to treat a bacterial infection selected from those described herein. The efficacy of the aforesaid combinations can be tested in animal models known in the art.

Exemplary immunomodulators that can be used in the combination therapies include, but are not limited to, e.g., afutuzumab (available from Roche®); pegfilgrastim (Neulasta®); lenalidomide (CC-5013, Revlimid®); thalidomide (Thalomid®), actimid (CC4047); and cytokines, e.g., IL-21 or IRX-2 (mixture of human cytokines including interleukin 1, interleukin 2, and interferon γ, CAS 951209-71-5, available from IRX Therapeutics).

Exemplary doses of such immunomodulators that can be used in combination with the antibacterial compounds of the invention include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

Examples of embodiments of the methods of using the antibacterial compounds of the invention in combination with an immunomodulator include these:

i. A method to treat a bacterial infection in a subject, comprising administering to the subject crystalline Compound (A) as described herein, and an immunomodulator.

ii. The method of embodiment i, wherein the immunomodulator is an activator of a costimulatory molecule or an inhibitor of an immune checkpoint molecule.

iii. The method of either of embodiments i and ii, wherein the activator of the costimulatory molecule is an agonist of one or more of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 and CD83 ligand.

iv. The method of any of embodiments i-iii above, wherein the inhibitor of the immune checkpoint molecule is chosen from PD-1, PD-L1, PD-L2, CTLA4, TIM3, LAG3, VISTA, BTLA, TIGIT, LAIR1, CD160, 2B4 and TGFR beta.

v. The method of any of any of embodiments i-iii, wherein the inhibitor of the immune checkpoint molecule is chosen from an inhibitor of PD-1, PD-L1, LAG-3, TIM-3 or CTLA4, or any combination thereof.

vi. The method of any of embodiments i-v, wherein the inhibitor of the immune checkpoint molecule is a soluble ligand or an antibody or antigen-binding fragment thereof, that binds to the immune checkpoint molecule.

vii. The method of any of embodiments i-vi, wherein the antibody or antigen-binding fragment thereof is from an IgG1 or IgG4 (e.g., human IgG1 or IgG4).

viii. The method of any of embodiments i-vii, wherein the antibody or antigen-binding fragment thereof is altered, e.g., mutated, to increase or decrease one or more of: Fc receptor binding, antibody glycosylation, the number of cysteine residues, effector cell function, or complement function.

ix. The method of any of embodiments i-viii, wherein the antibody molecule is a bispecific or multispecific antibody molecule that has a first binding specificity to PD-1 or PD-L1 and a second binding specifity to TIM-3, LAG-3, or PD-L2.

x. The method of any of embodiments i-ix, wherein the immunomodulator is an anti-PD-1 antibody chosen from Nivolumab, Pembrolizumab or Pidilizumab.

xi. The method of any of embodiments i-x, wherein the immunomodulator is an anti-PD-L1 antibody chosen from YW243.55.S70, MPDL3280A, MEDI-4736, MSB-0010718C, or MDX-1105.

xii. The method of any of embodiments i-x, wherein the immunomodulator is an anti-LAG-3 antibody molecule.

xiii. The method of embodiment xii, wherein the anti-LAG-3 antibody molecule is BMS-986016, xiv. The method of any of embodiments i-x, wherein the immunomodulator is an anti-PD-1 antibody molecule administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg., e.g., once a week to once every 2, 3, or 4 weeks.

xv. The method of embodiment xiv, wherein the anti-PD-1 antibody molecule is administered at a dose from about 10 to 20 mg/kg every other week.

xvi. The method of embodiment xv, wherein the anti-PD-1 antibody molecule, e.g., nivolumab, is administered intravenously at a dose from about 1 mg/kg to 3 mg/kg, e.g., about 1 mg/kg, 2 mg/kg or 3 mg/kg, every two weeks.

xvii. The method of embodiment xv, wherein the anti-PD-1 antibody molecule, e.g., nivolumab, is administered intravenously at a dose of about 2 mg/kg at 3-week intervals.

Compounds of the invention, particularly compounds of embodiments 1-12 described above, exhibit greater efficacy against important drug-resistant Gram-negative pathogens than hydroxamic acid compounds previously reported or improved off-target effect profiles; thus these compounds are especially useful to treat subjects with drug-resistant infections or avoid adverse side effects.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The present invention provides novel compounds, pharmaceutical formulations including the compounds, methods of inhibiting UDP-3-O—(R-3-hydroxydecanoyl)-N-acetyl-glucosamine deacetylase (LpxC), and methods of treating Gram-negative bacterial infections.

In another aspect, the invention provides a method of inhibiting a deacetylase enzyme in a Gram-negative bacterium, the method comprising the step of contacting the Gram-negative bacteria with the crystalline compound of the invention.

In still another aspect, the invention provides a method for treating a subject with a Gram-negative bacterial infection, the method comprising the step of administering to the subject in need thereof an antibacterially effective amount of crystalline Compound (A), optionally along with a pharmaceutically acceptable carrier.

The compounds of the invention can be administered by known methods, including oral, parenteral, inhalation, and the like. In certain embodiments, the compound of the invention is administered orally, as a pill, lozenge, troche, capsule, solution, or suspension. In other embodiments, a compound of the invention is administered by injection or infusion. Infusion is typically performed intravenously, often over a period of time between about 15 minutes and 4 hours. In other embodiments, a compound of the invention is administered intranasally or by inhalation; inhalation methods are particularly useful for treatment of respiratory infections. In other embodiments, a compound of the invention is administered intravenously, as by IV infusion, wherein the compound may be administered while it is dissolved in any suitable intravenous solution such as Ringer's lactate or an isotonic glucose or saline solution.

The compounds of the invention can be used for treating conditions caused by the bacterial production of endotoxin and, in particular, by Gram-negative bacteria and bacteria that use LpxC in the biosynthesis of lipopolysaccharide (LPS) or endotoxin.

The compounds of the invention also are useful in the treatment of patients suffering from or susceptible to respiratory tract infections (pneumonia, lung abscesses, bronchiectasis), bacteremia (sepsis), cystic fibrosis, skin and soft tissue infections (wound, surgical infections, complicated diabetic foot, complicated burns) complicated intraabdominal or complicated urinary track infections and sexually transmitted diseases caused by Gram-negative pathogens. The compounds of the invention also are useful in the conditions that are caused or exacerbated by the bacterial production of lipid A and LPS or endotoxin, such as sepsis, septic shock, systemic inflammation, localized inflammation, chronic obstructive pulmonary disease (COPD) and acute exacerbations of chronic bronchitis (AECB). For these conditions, treatment includes the administration of a compound of the invention, or a combination of compounds of the invention, optionally with a second agent wherein the second agent is a second antibacterial agent or a second non-antibacterial agent.

For sepsis, septic shock, systemic inflammation, localized inflammation, chronic obstructive pulmonary disease (COPD) and acute exacerbations of chronic bronchitis (AECB), preferred second non-antibacterial agents include antiendotoxins including endotoxin receptor-binding antibodies, endotoxin-binding antibodies, antiCD14-binding protein antibodies, antilipopolysaccharide-binding protein antibodies and tyrosine kinase inhibitors.

In treatment of serious or chronic respiratory tract infections, the compounds of the present invention may also be used with second non-antibacterial agents administered via inhalation. Preferred non-antibacterial agents used in this treatment include anti-inflammatory steroids, non-steroidal anti-inflammatory agents, bronchiodilators, mucolytics, anti-asthma therapeutics and lung fluid surfactants. In particular, the non-antibacterial agent may be selected from a group consisting of albuterol, salbuterol, budesonide, beclomethasone, dexamethasone, nedocromil, beclomethasone, fluticasone, flunisolide, triamcinolone, ibuprofin, rofecoxib, naproxen, celecoxib, nedocromil, ipratropium, metaproterenol, pirbuterol, salneterol, bronchiodilators, mucolytics, calfactant, beractant, poractant alfa, surfaxin and pulmozyme (also called domase alfa).

The compound of the invention can be used, alone or in combination with a second antibacterial agent for the treatment of a serious or chronic respiratory tract infection including serious lung and nosocomial infections such as those caused by *Enterobacter aerogenes, Enterobacter cloacae, Escherichia coli, Klebsiella pneumoniae, Klebsiella oxytoca, Proteus mirabilis, Serratia marcescens, Stenotrophomonas maltophilia, Pseudomonas aeruginosa, Burkholderia cepacia, Acinetobacter baumanii, Alcaligenes xylosoxidans, Flavobacterium meningosepticum, Providencia stuartii* and *Citrobacter freundi*, community lung infections such as those caused by *Haemophilus influenzae, Legionella species, Moraxella catarrhalis, Enterobacter species, Acinetobacter species, Klebsiella species*, and *Proteus* species, and infections caused by other bacterial species such as *Neisseria* species, *Shigella* species, *Salmonella* species, *Helicobacter pylori, Vibrionaceae* and *Bordetella* species as well as the infections is caused by a *Brucella* species, *Francisella tularensis* and/or *Yersinia pestis*.

A compound of the present invention may also be used in combination with other agents (combination partners), e.g., an additional antibiotic agent other than Compound (A), for treatment of a bacterial infection in a subject.

By the term "combination", is meant either a fixed combination in one dosage unit form, as separate dosage forms suitable for use together either simultaneously or sequentially, or as a kit of parts for the combined administration where a compound of the present invention and a combination partner may be administered independently at the same time or separately within time intervals that especially allow that the combination partners show a cooperative, e.g., synergistic, effect, or any combination thereof.

When used for treating Gram-negative bacteria, the compounds of the present invention can sensitize Gram-negative bacteria to the effects of a second agent, thus they may be used in combinations or in combination therapies with other antibacterial agents.

In certain embodiments of the present invention, a compound of the present invention is used in combination with a second antibacterial agent; non-limiting examples of second antibacterial agents for such use may be selected from the following groups:

(1) Macrolides or ketolides such as erythromycin, azithromycin, clarithromycin, and telithromycin;

(2) Beta-lactams including penicillin such as penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cephalosporin such as cepalothin, cephapirin, cephradine, cephaloridine, cefazolin, cefamandole, cefuroxime, cephalexin, cefprozil, cefaclor, loracarbef, cefoxitin, cefinetazole, cefotaxime, ceftizoxime, ceftriaxone, cefoperazone, ceftazidime, cefixime, cefpodoxime, ceftibuten, cefdinir, cefpirome, cefepime, and carbapenems such as carbapenem, imipenem, meropenem and PZ-601;

(3) Monobactams such as aztreonam;

(4) Quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, ganefloxacin, gemifloxacin and pazufloxacin;

(5) Antibacterial sulfonamides and antibacterial sulphanilamides, including para-aminobenzoic acid, sulfadiazine, sulfisoxazole, sulfamethoxazole and sulfathalidine;

(6) Aminoglycosides such as streptomycin, neomycin, kanamycin, paromycin, gentamicin, tobramycin, amikacin, netilmicin, spectinomycin, sisomicin, dibekalin and isepamicin;

(7) Tetracyclines such as tetracycline, chlortetracycline, demeclocycline, minocycline, oxytetracycline, methacycline, doxycycline, tegacycline;

(8) Rifamycins such as rifampicin (also called rifampin), rifapentine, rifabutin, bezoxazinorifamycin and rifaximin;

(9) Lincosamides such as lincomycin and clindamycin;

(10) Glycopeptides such as vancomycin and teicoplanin;

(11) Streptogramins such as quinupristin and daflopristin;

(12) Oxazolidinones such as linezolid and tedizolid;

(13) Polymyxin, colistin and colymycin;

(14) Trimethoprim and bacitracin.

(15) Efflux pump inhibitors.

The second antibacterial agent may be administered in combination with the compound of the present inventions, wherein the second antibacterial agent is administered prior to, simultaneously with, or after the compound or compounds of the present invention. When simultaneous administration of a compound of the invention with a second agent is desired and the route of administration is the same, then a compound of the invention may be formulated with a second agent into the same dosage form. An example of a dosage form containing a compound of the invention and a second agent is a tablet or a capsule.

In some embodiments, a combination of a compound of the invention and a second antibacterial agent may provide synergistic activity. For example, use of a compound of the invention with vancomycin or a cephalosporin may be synergistic; thus in some embodiments, the compound of the invention is used in combination with vancomycin or a cephalosporin, typically by infusion. The compound of the invention and second antibacterial agent may be administered together, separate but simultaneously, or sequentially.

When used for treating serious or chronic respiratory tract infections, the compound of the invention may be used alone or in combination with a second antibacterial agent; in some embodiments, the second antibacterial agent is administered via inhalation. Optionally, the combination may be administered as a single composition by inhalation. In the case of administration by inhalation, a suitable second antibacterial agent is selected from the group consisting of tobramycin, gentamicin, aztreonam, ciprofloxacin, polymyxin, colistin, colymycin, vancomycin, cephalosporins, azithromycin and clarithromycin. Vancomycin is sometimes preferred.

An "effective amount" of a compound is that amount necessary or sufficient to treat or prevent a bacterial infection and/or a disease or condition described herein. In an example, an effective amount of Compound (A) is an amount sufficient to treat bacterial infection in a subject. In another example, an effective amount of the LpxC inhibitor is an amount sufficient to treat a bacterial infection, such as, but not limited to *Pseudomonas aeruginosa* and the like, in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of a bacterial infection. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

Compounds of the invention may be used in the treatment of states, disorders or diseases as described herein, or for the manufacture of pharmaceutical compositions for use in the treatment of these diseases. The invention provides methods of use of compounds of the present invention in the treatment of these diseases or for preparation of pharmaceutical compositions having compounds of the present invention for the treatment of these diseases.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of Compound (A) as active ingredient in combination with a pharmaceutically acceptable carrier, or optionally two or more pharmaceutically acceptable carriers.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Typically, pharmaceutically acceptable carriers are sterilized and/or substantially pyrogen-free.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, inhalation, topical, transdermal, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored base, for example, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable carriers such as sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, glycol ethers, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Intravenous infusion is sometimes a preferred method of delivery for compounds of the invention. Infusion may be used to deliver a single daily dose or multiple doses. In some embodiments, a compound of the invention is administered by infusion over an interval between 15 minutes and 4 hours, typically between 0.5 and 3 hours. Such infusion may be used once per day, twice per day or up to three times per day.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated effects, will range from about 0.0001 to about 100 mg per kilogram of body weight per day, frequently from about 0.01 to about 50 mg per kg per day, and often from about 1.0 to about 50 mg per kg per day. Total daily dosage by intravenous administration is typically 1-4 grams/day for a typical subject (e.g., a 70 kg human subject); total daily dosage by inhalation would typically be 50-500 mg per day, or about 100-200 mg. An effective amount is that amount treats a bacterial infection.

If desired, the effective daily dose of the active compound may be administered as one, two, three, four, five, six or more sub-doses administered separately at appropriate intervals throughout the day, optionally, in unit dosage forms. Compounds delivered orally or by inhalation, are commonly administered in one to four doses per day. Compounds delivered by injection are typically administered once per day, or once every other day. Compounds delivered intravenously are typically administered in one to three doses per day.

In accordance with the foregoing the present invention provides in a yet further aspect:

A pharmaceutical combination comprising a crystalline compound (A), and b) a co-agent, e.g. a second drug agent as defined above.

A method as defined above comprising co-administration, e.g. concomitantly or in sequence, of a therapeutically effective amount of crystalline compound (A) and a co-agent, e.g. a second therapeutic agent as defined above.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time. Fixed combinations are also within the scope of the present invention. The administration of a pharmaceutical combination of the invention results in a beneficial effect, e.g. a synergistic therapeutic effect, compared to a monotherapy applying only one of its pharmaceutically active ingredients.

Each component of a combination according to this invention may be administered separately, together, or in any combination thereof.

The compound of the invention and any additional agent may be formulated in separate dosage forms. Alternatively, to decrease the number of dosage forms administered to a patient, the compound of the invention and any additional agent may be formulated together in any combination. For example, the compound of the invention inhibitor may be formulated in one dosage form and the additional agent may be formulated together in another dosage form. Any separate dosage forms may be administered at the same time or different times.

Alternatively, a composition of this invention comprises an additional agent as described herein. Each component may be present in individual compositions, combination compositions, or in a single composition.

EXAMPLES

The invention is further illustrated by the following examples, which should not be construed as limiting. The assays used throughout the Examples are well established in the art: demonstration of efficacy in these assays is generally regarded as predictive of efficacy in subjects.

ABBREVIATIONS

Ac acetyl
ACN Acetonitrile
AcOEt/EtOAc Ethyl acetate
AcOH acetic acid
aq aqueous
CDI Carbonyldiimidazole
$CH_3CN$ Acetonitrile
DBU 1,8-Diazabicyclo[5.4.0]-undec-7-ene
$Boc_2O$ di-tert-butyl dicarbonate
DCE 1,2-Dichloroethane
DCM Dichloromethane
DiBAl-H Diisobutylaluminum Hydride
DIPEA N-Ethyldiisopropylamine
DMAP Dimethylaminopyridine
DMF N,N'-Dimethylformamide
DMSO Dimethylsulfoxide
EI Electrospray ionisation
$Et_2O$ Diethylether
$Et_3N$ Triethylamine
Ether Diethylether
EtOAc Ethylacetate
EtOH Ethanol
FC Flash Chromatography
h hour(s)
HATU O-(7-Azabenzotriazole-1-yl)-N,N,N'N'-tetramethyluronium hexafluorophosphate
HBTU O-(Benzotriazol-1-yl)-N,N,N',N'-tetramethyluronium hexafluorophosphate
HCl Hydrochloric acid
HMPA Hexamethylphosphoramide
HOBt 1-Hydroxybenzotriazole
HPLC High Performance Liquid Chromatography
$H_2O$ Water
L liter(s)
LC-MS Liquid Chromatography Mass Spectrometry
LiHMDS Lithium bis(trimethylsilyl)amide
$MgSO_4$ Magnesium Sulfate
Me methyl
MeI Iodomethane
MeOH Methanol
mg milligram
min minute(s)
mL milliliter
MS Mass Spectrometry
$NaHCO_3$ Sodium Bicarbonate
$Na_2SO_4$ Sodium Sulfate
$NH_2OH$ hydroxylamine
Pd/C palladium on charcoal
$Pd(OH)_2$ palladium hydroxide
PG protecting group
Ph phenyl
$Ph_3P$ triphenyl phosphine
Prep Preparative
Rf ratio of fronts
RP reverse phase
Rt Retention time
rt Room temperature
$SiO_2$ Silica gel
$SOCl_2$ Thionyl Chloride
TBAF Tetrabutylammonium fluoride
TBDMS t-Butyldimethylsilyl
TEA Triethylamine
TFA Trifluoroacetic acid
THF Tetrahydrofuran
TLC Thin Layer Chromatography
TsCl toluene sulfonyl chloride
General Conditions:

Mass spectra were run on LC-MS systems using electrospray ionization. These were WATERS Acquity Single Quard Detector. [M+H]$^+$ refers to mono-isotopic molecular weights.

NMR spectra were run on open access Varian 400 or Varian 500 NMR spectrometers. Spectra were measured at 298K and were referenced using the solvent peak. Chemical shifts for $^1$H NMR are reported in parts per million (ppm).

Mass spectra were run on LC-MS systems with one of the following conditions:
1. Waters Acquity UPLC-H class system equipped with SQD detector.
   Column: ACQUITY UPLC HSS C18 (50*2.1) mm, 1.8u.
   Column temperature: Ambient.
   Mobile Phase: A) 0.1% FA+5 mM Ammonium Acetate in Water.
   B) 0.1% FA in Acetonitrile.
   Gradient: 5-5% solvent B in 0.40 min, 5-35% solvent B in 0.80 min, 35-55% solvent B in 1.2 min, 55-100% solvent B in 2.5 min.
   Flow rate: 0.55 mL/min.
   Compounds were detected by a Waters Photodiode Array Detector.

2. Waters LCMS system equipped with ZQ 2000 detector.
   Column: X-BRIDGE C18 (50*4.6) mm, 3.5u.
   Column temperature: Ambient.
   Mobile Phase: A) 0.1% NH3 in Water.
     B) 0.1% NH3 in Acetonitrile.
   Gradient: 5-95% solvent B in 5.00 min.
   Flow rate: 1.0 mL/min.
   Compounds were detected by a Waters Photodiode Array Detector.
3. Waters ACQUITY UPLC system and equipped with a ZQ 2000 MS system.
   Column: Kinetex by Phenomenex, 2.6 um, 2.1×50 mm
   Column temperature: 50° C.
   Gradient: 2-88% (or 00-45%, or 65-95%) solvent B over a 1.29 min period
   Flow rate: 1.2 mL/min.
   Compounds were detected by a Waters Photodiode Array Detector.

I.1. Synthesis of (R)-4-(5-(cyclopropylethynyl)isoxazol-3-yl)-N-hydroxy-2-methyl-2-(methylsulfonyl) butanamide [A]

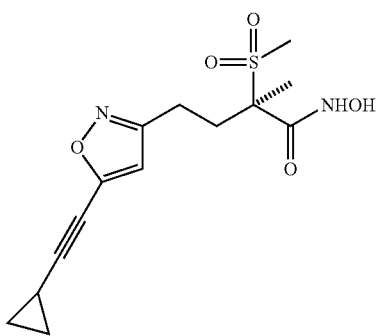

(A)

Method A

Step 1. Synthesis of (cyclopropylbuta-1,3-diyn-1-yl)trimethylsilane [1.1a]

To a solution of (bromoethynyl)cyclopropane (60 g, 414 mmol) in piperidine (345 ml) at 0° C. was added ethynyltrimethylsilane (44.7 g, 455 mmol) and CuI (7.88 g, 41.4 mmol). The solution was then stirred at rt for 2 hours. The reaction was quenched by adding sat. aq. NH$_4$Cl solution and then extracted with TBME. The organic layer was washed with water, brine, dried over MgSO$_4$ and concentrated. The crude material was purified by silica gel column chromatography, heptane as eluant to give product (42 g, 62% yield). $^1$H NMR (400 MHz, CDCl$_3$) 0.13-0.24 (m, 9 H) 0.72-0.91 (m, 4 H) 1.25-1.36 (m, 1 H)

Step 2. Synthesis of ethyl 5-chloro-5-(hydroxyimino)-2-methyl-2-(methylsulfonyl)pentanoate [1.1b]

NCS (10.8 g, 81 mmol, 1.2 equiv) was added to a solution of ethyl 5-(hydroxyimino)-2-methyl-2-(methylsulfonyl)pentanoate (17 g, 67.6 mmol) in DMF (34 mL) and the resulting mixture was stirred at rt for 3 hours. The solvent was then removed under vacuum. The residue was dissolved in EtOAc, washed with water, brine, dried over Na$_2$SO$_4$ and concentrated to afford product (19 g, 98% yield). The crude material was continued to the next step with no further purification. LCMS (m/z): 286.2 [M+H]$^+$.

Step 3. Synthesis of (R)-ethyl 4-(5-(cyclopropylethynyl)isoxazol-3-yl)-2-methyl-2-(methylsulfonyl) butanoate [1.1c]

To a solution of 1.1a (8.4 g, 51.8 mmol) in MeOH (25 mL) was added K$_2$CO$_3$ (14.3 g, 104 mmol) and the mixture was stirred at rt for 18 hours. The mixture was then diluted with CH$_2$Cl$_2$ (75 mL) and filtered. The filtrate was then placed in an ice-water bath and 1.1.b (14.79 g, 51.8 mmol) was added. TEA (14.43 ml, 104 mmol) was then added to the above solution over 30 mins and the mixture was stirred at rt for 4 hours. The solvent was removed under reduced pressure. The residue was diluted with TBME and washed with water, brine, dried over Na$_2$SO$_4$ and concentrated. The residue was purified by silica gel column chromatography, EtOAc/heptane 0 to 60%, to give (±)-1.1c (9.0 g, 51%). The two enantiomers were separated by chiral HPLC.

Separation condition: Chiral AD column; flow rate: 30 ml/min; solvent: Heptane/EtOH=50/50; pressure 1263 psi. Product 1: tR 3.76 min, product 2: tR 4.73 min. Product 2 is the desired isomer 1.1c (3.0 g). $^1$H NMR (400 MHz, CDCl$_3$) 0.84-1.08 (m, 4 H) 1.32 (t, J=7.14 Hz, 3 H) 1.45-1.56 (m, 2 H) 1.68 (s, 3 H) 2.17 (s, 1 H) 2.25-2.40 (m, 1 H) 2.53-2.71 (m, 2 H) 2.80 (d, J=5.04 Hz, 1 H) 3.05 (s, 3 H) 4.27 (q, J=7.11 Hz, 2 H) 6.17 (s, 1 H). LCMS (m/z): 340.3 [M+H]$^+$.

Step 4. Synthesis of (R)-4-(5-(cyclopropylethynyl) isoxazol-3-yl)-2-methyl-2-(methylsulfonyl)butanoic acid [1.1d]

LiOH.H$_2$O (0.3 g, 2.0 mmol) was added to a solution of 1.1c (1.2 g, 3.5 mmol) in THF/MeOH/water (12 mL, 1/1/1) and the resulting solution was stirred at rt for 1 hour. The solvent was then removed under reduced pressure. The remaining material was acidified with 3.0 N HCl aq. solution and extracted with EtOAc. The organic layer was washed with brined, dried over Na$_2$SO$_4$ and concentrated to give product (1.1 g, quantitative yield). The crude material was continued to the next step with no further purification. LCMS (m/z): 312.3 [M+H]$^+$.

Step 5. Synthesis of (2R)-4-(5-(cyclopropylethynyl) isoxazol-3-yl)-2-methyl-2-(methylsulfonyl)-N-((tetrahydro-2H-pyran-2-yl)oxy)butanamide [1.1e]

To a solution of 1.1d (1.1 g, 3.53 mmol) in DMF (6 mL) at rt was added aza-HOBt (0.866 g, 6.36 mmol), EDC (1.016 g, 5.30 mmol), and O-(tetrahydro-2H-pyran-2-yl)hydroxylamine (0.621 g, 5.30 mmol), TEA (1.477 ml, 10.60 mmol). The solution was stirred at 45° C. for 3 hours then rt for 18 hours. The solvent was removed under reduced pressure. The residue was diluted with EtOAc, washed with sat. aq. NaHCO$_3$ solution. The organic layer was washed with brine, dried over Na$_2$SO$_4$ and concentrated. The residue was purified by silica gel column chromatography, EtOAc/heptane 0 to 70% to give product 1.2 g (83% yield). LCMS (m/z): 411.3 [M+H]$^+$.

Step 6. Synthesis of (R)-4-(5-(cyclopropylethynyl)isoxazol-3-yl)-N-hydroxy-2-methyl-2-(methylsulfonyl)butanamide [A]

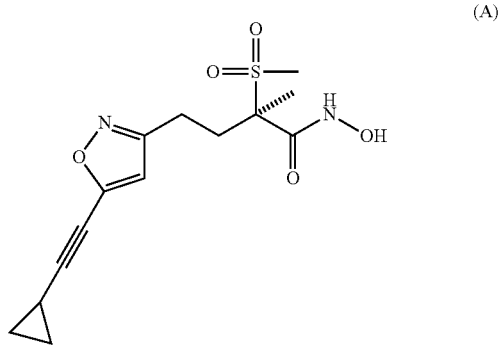 [SMILES: C[C@@](CCc1cc(C#CC2CC2)on1)(C(=O)NO)S(C)(=O)=O]

(A)

To a solution of 1.1e (1.2 g, 2.92 mmol) in MeOH (5.0 mL) and DCM (5.0 mL) at 0° C. was added HCl (0.731 mL, 4.0 M in dioxane, 2.92 mmol). The solution was stirred at rt for 1 hour. The solvent was then removed under reduced pressure. The remaining material was purified by silica gel column chromatography, acetone/heptane 0 to 60% to give product 0.79 g (81% yield). $^1$H NMR (400 MHz, DMSO): 10.97 (s, 1H), 9.24 (s, 1H), 6.73 (s, 1H), 3.06 (s, 3H), 2.71 (dd, J=17.3, 9.1 Hz, 1H), 2.56 (d, J=4.0 Hz, 1H), 2.47-2.40 (m, 1H), 2.06-1.95 (m, 1H), 1.69 (ddd, J=13.3, 8.3, 5.0 Hz, 1H), 1.50 (s, 3H), 0.99 (td, J=6.8, 4.0 Hz, 2H), 0.88-0.82 (m, 2H). LCMS (m/z): 327.3 [M+H]$^+$.

Material produced in this way was essentially pure, but was amorphous and did not exhibit a distinct melting point. It was also deliquescent, i.e. it absorbed water when exposed to air to a noticeable extent, and it tended to darken on standing at ambient temperature. This material required special handling and was not considered suitable for development as a pharmaceutical.

Method B

Alternative Synthesis of 1.1c

Step 7. Synthesis of ethyl 2-methyl-2-(methylsulfonyl)hex-5-enoate [1.1f]

To a solution of ethyl 2-(methylsulfonyl)propanoate (50 g, 277 mmol) in DMF (277 ml) at 0° C. was added NaH (14.43 g, 60%, 361 mmol) and the mixture was stirred at rt for 2 hours. The mixture was then cooled at 0° C. and 4-bromobut-1-ene (41.2 g, 305 mmol) was added over 30 mins. The mixture was then stirred at rt for 18 hours. The solvent was removed under high vacuum. To the residue was added TBME and then quenched with sat. aq. NH$_4$Cl solution. The phases were separated and the aqueous layer was extracted with TBME. The combined organic layer was washed with brine and concentrated. The residue was purified by silica gel column chromatography, EtOAc/heptane 0 to 50% to give product. $^1$H NMR (400 MHz, CDCl$_3$): 1.32 (t, J=7.14 Hz, 3 H) 1.62 (s, 3 H) 1.91-2.06 (m, 2 H) 2.12-2.42 (m, 2 H) 3.04 (s, 3 H) 4.28 (q, J=7.14 Hz, 2 H) 4.92-5.14 (m, 2 H) 5.64-5.86 (m, 1 H)

Step 8. Separation of 1.1f to Provide 1.1f-I and 1.1f-II

The racemic material 1.1f was separated into enantiomer 1.1f-I and 1.1f-I and 1.1f-II by simulated moving bed chromatography.

| Instrumentation | BAYCC50 SMB unit |
|---|---|
| Flow rate | Eluent: 13.58 L/h |
| | Feed: 0.53 L/h |
| | Extract: 11.2 L/h |
| | Raffinate: 2.9 L/h |
| | Recycle: 24.00 L/h |
| Mobile phase | Heptane:EtOH 80:20 |
| Column | Chiralpak AD 20 uM 8 × (100 × 50 mm) |
| Switch time | 71 sec |
| Temperature | 25° C. |
| Peak 1 | 5.5 min |
| Peak 2 | 8.9 min |

The second peak is the desired isomer ethyl (R)-2-methyl-2-(methylsulfonyl)hex-5-enoate 1.1f-II

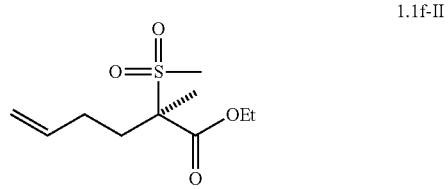

1.1f-II

Step 9. Synthesis of ethyl (R)-2-methyl-2-(methylsulfonyl)-5-oxopentanoate [1.1g]

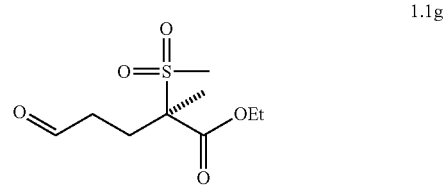

1.1g

To a solution of 1.1f-II (6 g, 25.6 mmol) in dioxane (128 mL) and water (43 mL) was added 2,6-lutidine (5.49 g, 51.2 mmol) and OsO$_4$ (3.25 g, 4% in water, 0.512 mmol). After 30 mins, the solution was placed in an ice water bath and NaIO$_4$ (21.91 g, 102 mmol) was added. The mixture was then stirred at rt for 18 hours. The mixture was then filtered and the filtrate was concentrated. The residue was dissolved in EtOAc and washed with 1.0 HCl aq solution, brine, dried over Na$_2$SO$_4$ and concentrated. The crude material was continued to the next step with no further purification. $^1$H NMR (400 MHz, Solvent): 1.32 (t, J=7.14 Hz, 3 H) 1.61 (s, 3 H) 2.22-2.36 (m, 1 H) 2.43-2.62 (m, 2 H) 2.63-2.76 (m, 1 H) 3.07 (s, 3 H) 4.28 (q, J=7.14 Hz, 2 H) 9.69-9.92 (m, 1 H)

Step 10. Synthesis of ethyl (R)-5-(hydroxyimino)-2-methyl-2-(methylsulfonyl)pentanoate [1.1h]

To a solution of hydroxylamine hydrochloride (2.0 g, 28.2 mmol) in Water (26 mL) was added NaHCO$_3$ (2.4 g). After stirring at rt for 10 mins, a solution of 1.1 g (6.0 g, 25 mmol) in EtOH (26 mL) was added and the solution was stirred at rt for 18 hours. The solvent was removed under reduced pressure. The remaining material was extracted with EtOAc. The organic layer was washed with brine, dried over Na$_2$SO$_4$ and concentrated to give product 6.4 g. The crude material was continued to the next step with no further purification. LCMS (m/z): 252.1 [M+H]$^+$.

Step 11. Synthesis of Synthesis of (R)-ethyl 4-(5-(cyclopropylethynyl)isoxazol-3-yl)-2-methyl-2-(methylsulfonyl)butanoate [1.1c]

Compound 1.1c was synthesized from 1.1h by the procedure of example 1.1 step 2-3. The chiral separation in step 3 is unnecessary since 1.1h is enantiomerically pure.

Preparation of Crystalline Compound (A)

1501 mg Compound A in amorphous free acid form was dissolved in 5 mL DCM at 25° C. and slowly added to 20 mL heptane over a period of 5 hours at 55° C. Oil-like precipitation adhered to the container wall at the beginning and therefore, magnetic stirring was used instead of the mechanical agitator for 1 hour at 300 r.p.m. The obtained suspension was kept at 55° C. for 20 hours using mechanical agitation at 500 r.p.m. The solids were filtered at ambient condition and then dried at 60° C. for 12 hours. 1213 mg of crystalline Compound (A) was obtained, a yield of about 81%.

Figure 2:
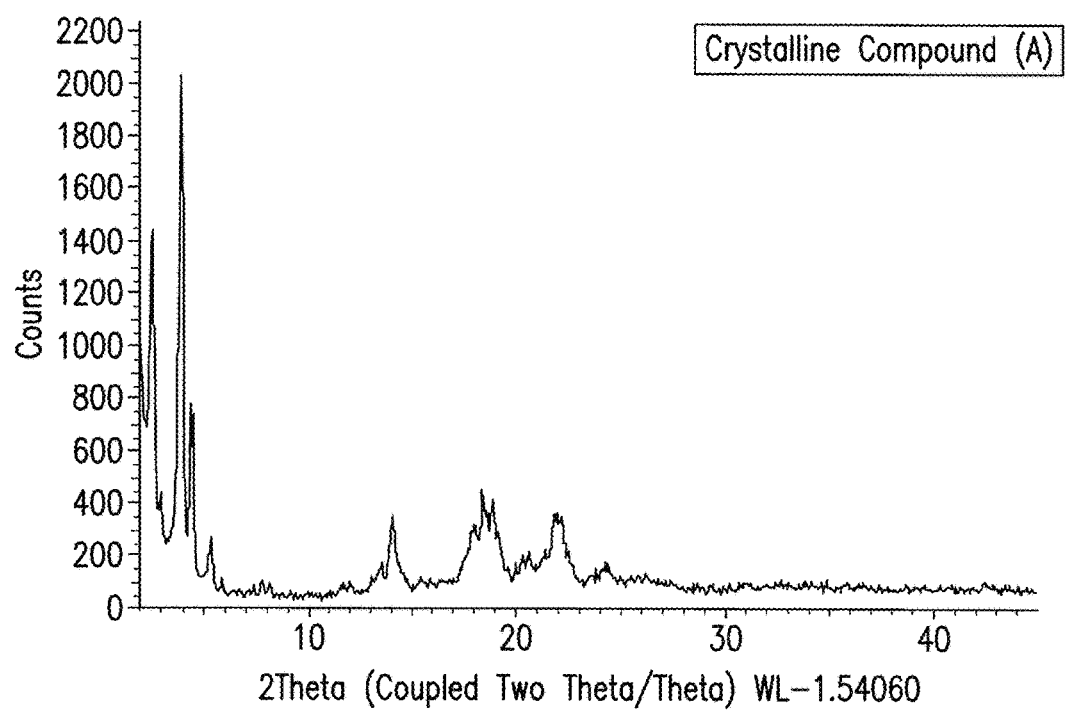
FIG. 2. XRPD of Crystalline Compound.
Figure 3:
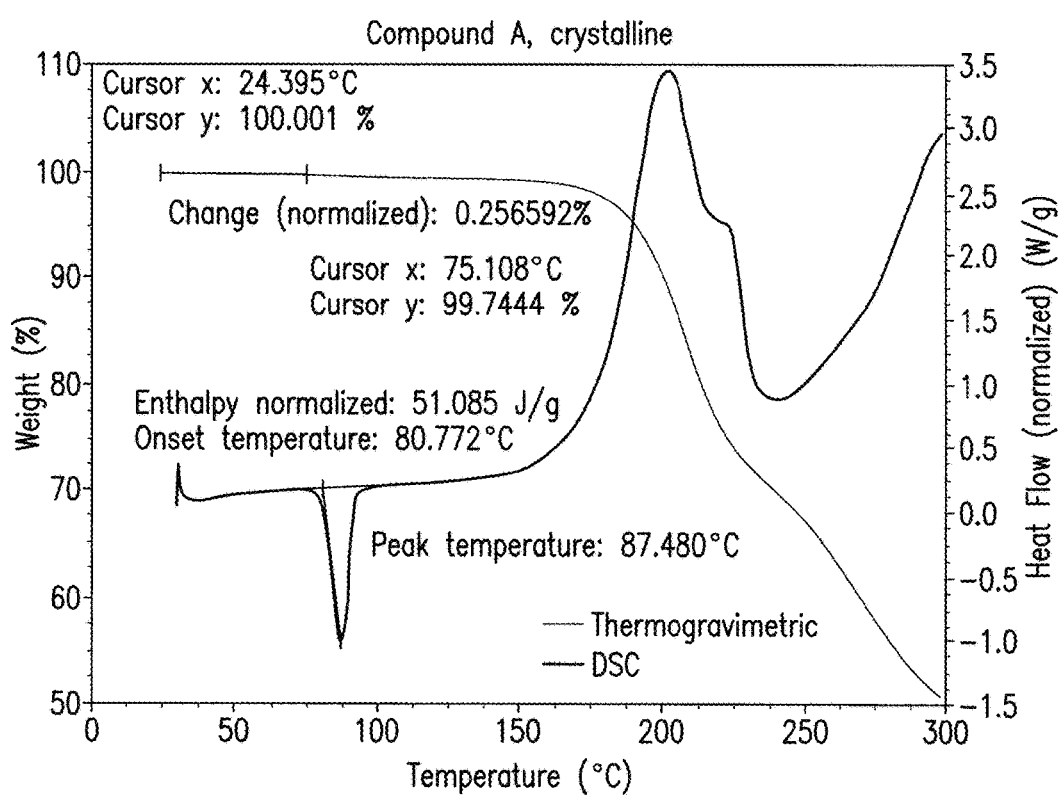
FIG. 3. Thermogravimetric Analysis and Differential Scanning Calorimetry Analysis of Crystalline Compound A.
Figure 4:
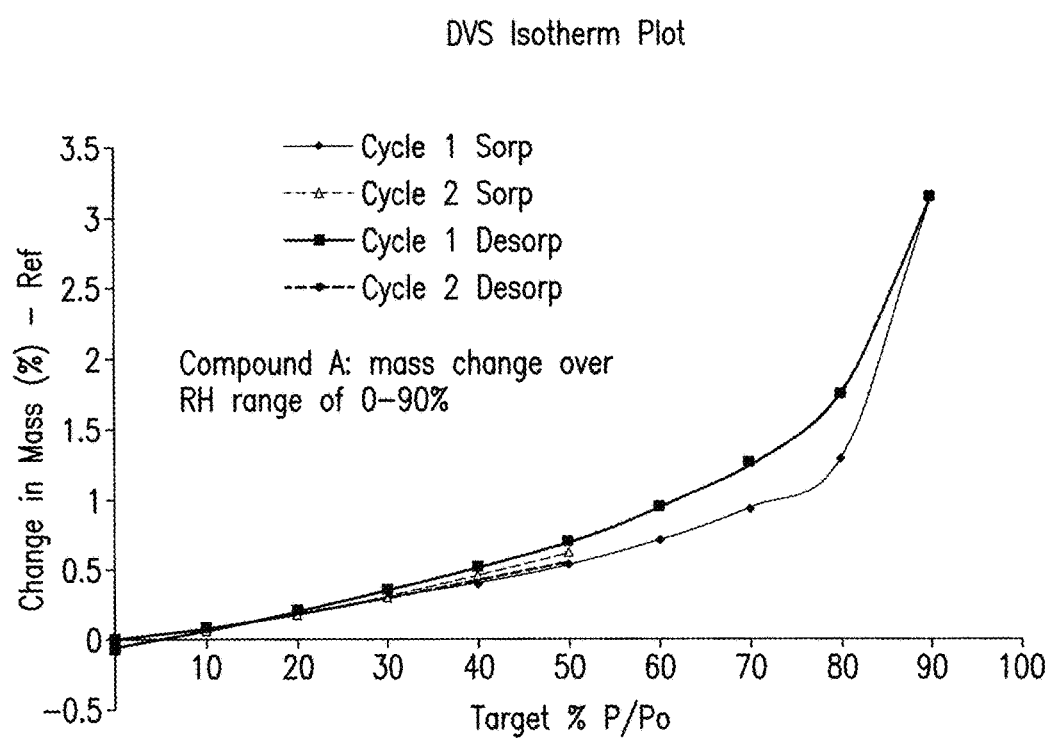
FIG. 4. Isotherm Plots showing reversible mass changes of Crystalline Compound A over a Relative Humidity range of 0-90%.

This material has the appearance of rod-like crystals (see FIG. 1) and exhibits a reasonably sharp melting point peaking at 80.8° C. Unlike the amorphous material, which was significantly deliquescent at humidity of about 80% or higher, the crystalline product has low hygroscopicity: its mass increased by 1.3% at relative humidity (RH) of 80%, and by 3.2% at RH=90%. The XRPD spectrum for this crystalline material is shown in FIG. 2 (WL=1.54060). This data was collected with a Bruker D8 Advance defice, using a LYNXEYE detector (1D mode); open angle 1.198°, slit opening 5 mm, using Cu Kalpha wavelength (0.15406 nm), 40 kV X-ray generator at 4 mAmp, step size 0.041 degrees, 2° to 45° 2theta value; scan time 2162 seconds. Primary soller slit 2.5°; secondary soller slit 2.5°; divergent slit 0.6 mm; antiscatter slit 5.0 mm.

The table below provides a peak listing for the XRPD spectrum, diffraction angles (2Theta) reported in degrees.

| Angle | d Value | Rel. Intensity |
|---|---|---|
| 3.889 | 22.69933 | 100.0% |
| 2.542 | 34.73140 | 38.8% |
| 4.403 | 20.05238 | 38.6% |
| 18.437 | 4.80827 | 12.0% |
| 14.004 | 6.31908 | 12.0% |
| 18.820 | 4.71137 | 11.8% |
| 18.769 | 4.72410 | 11.3% |
| 5.281 | 16.71928 | 10.6% |
| 21.840 | 4.06615 | 9.8% |
| 22.069 | 4.02458 | 8.4% |
| 18.020 | 4.91881 | 7.5% |
| 14.287 | 6.19433 | 4.7% |
| 13.439 | 6.58317 | 4.4% |
| 20.566 | 4.31507 | 3.1% |
| 7.733 | 11.42390 | 2.9% |
| 5.845 | 15.10742 | 2.0% |
| 2.891 | 30.53256 | 1.7% |
| 8.138 | 10.85606 | 1.5% |

In one embodiment, the crystal form is characterized by XRPD peaks at diffraction angles (2Theta) of 3.9 and 2.5 and 4.4 and 18.4 and 14.0 degrees. This embodiment can be further characterized by one or more additional XRPD peaks at diffraction angles (2Theta) of 18.8 and/or 5.3 degrees and/or 21.8 degrees and/or 22.1 degrees and/or 18.0 degrees.

Pharmaceutical Activity

P. aeruginosa LpxC Inhibition Assay

The *P. aeruginosa* LpxC protein is produced according to the general method of Hyland et al (Journal of Bacteriology 1997 179, 2029-2037: Cloning, expression and purification of UDP-3-O-acyl-GlcNAc deacetylase from *Pseudomonas aeruginosa*: a metalloamidase of the lipid A biosynthesis pathway). The LC-MS/MS method for quantitation of LpxC product was developed using an Agilent 1200 Capillary HPLC system coupled to an Applied Biosystems MDS Sciex 4000QTRAP mass spectrometer. Both instruments are controlled using the Applied Biosystems MDS Sciex Analyst software. LpxC reaction product (UDP-3-O—(R-3-hydroxyacyl)-glucosamine) was produced by hydrolysis of LpxC substrate catalyzed by P.a. LpxC and purified using reversed phase chromatography on a Phenomenex Luna C18(2) 4.6×50 mm column. An LpxC product calibration curve was generated to evaluate the sensitivity and dynamic range of the LC-MS/MS method. Briefly, compounds are pre-incubated with 1 nM *P. aeruginosa* LpxC for 30 min. at room temperature. Reactions are initiated by the addition of 2 μM UDP-3-O—(R-3-hydroxydecanoyl)-GlcNAc. Reactions are conducted in a 384-well plate with a total volume of 50 μL in each well containing 50 mM Sodium phosphate pH 7.5, 0.005% Trition X-100 for 20 min at room temperature. After quenching with 1.8% HOAc (5 μL of a 20% HOAc added to each well), reaction mixtures are analyzed using the LC-MS/MS method and peak areas are transformed into product concentration using a LpxC product calibration curve. Total activity (0% inhibition control) is obtained from reactions with no inhibitors and 100% inhibition control is the background using quenched samples before reaction starts. For $IC_{50}$ determinations, peak areas are converted to percent inhibition in Microsoft Excel. Percent inhibition values are plotted vs. log compound concentration using XLfit. Data is fit to the four-parameter logistic equation using the non-linear regression algorithm in XLfit to return the $IC_{50}$ and hill slope values.

Bacterial Screens and Cultures

Bacterial isolates were cultivated from −70° C. frozen stocks by two consecutive overnight passages at 35° C. in ambient air on 5% blood agar (Remel, Lenexa, Kans.). Quality control strain, *P. aeruginosa* ATCC 27853, *A. baumannii* ATCC19606 and *E. coli* ATCC 25922 are from the American Type Culture Collection (ATCC; Rockville, Md.) and PAO1 was received from Dr. K. Poole.

Susceptibility Testing

Minimal Inhibitory Concentrations (MICs) were determined by the broth microdilution method in accordance with Clinical and Laboratories Institute (CLSI) guidelines (CLSI M100-S25, Performance Standards for Antimicrobial Susceptibility Testing; Twenty-fifth Informational Supplement). In brief, fresh bacterial overnight cultures were resuspended in sterile saline, adjusted to a 0.5 McFarland turbidity standard and then diluted 2000-fold in cation adjusted Mueller-Hinton Broth II (MHB; Remel BBL) to yield a final inoculum of approximately $5 \times 10^5$ colony-forming units (CFU)/mL. Two-fold serial dilutions of compounds were prepared in 100% dimethyl sulfoxide (DMSO) at 100-fold the highest final assay concentration; the resulting dilution series of compounds were diluted 1:10 with sterile water. Ten μl of the drug dilution series in 10% DMSO was transferred to microtiter wells and 90 μl of bacterial suspension was inoculated into the wells. For testing the ability of compounds to potentiate the activity of known antibiotics, the assay was modified as follows; known antibiotics were added to the bacterial inoculum at 1.1-fold the final assay concentration indicated in Table A. All inoculated microdilution trays were incubated in ambient air at 35° C. for 20 hours. Following incubation, assay plates were read in a microtiter plate reader at 600 nm and visually inspected to confirm the MIC endpoint well with the OD value. The lowest concentration of the compound that prevented visible growth was recorded as the MIC. Performance of the assay was monitored by testing ciprofloxacin against the laboratory quality control strain in accordance with guidelines of the CLSI.

The LpxC inhibitory activity for selected compounds of the invention on LpxC from *P. aeruginosa* are reported in Table A. The MIC assays for *P. aeruginosa*, *E. coli* and *A. baumannii* were also performed in the presence of sub-inhibotory concentrations of rifampicin to demonstrate the potential for synergy with other antimicrobial agents—see Table B.

TABLE A

Biological Data

| Compound number | P.A. LpxC IC$_{50}$ [µmol l$^{-1}$] |
|---|---|
| A | 0.003 |

TABLE B

Antibacterial Efficacy and Synergy Data

| Cmpd No. | P.A. PAO1 NB52019 MIC (µg/ml) | E.C. ATCC 25922 MIC (µg/ml) | E.C. ATCC 29522 (+2 µg/ml RIF) MIC (µg/ml) | A.B. ATCC 19606 MIC (µg/ml) | A.B. ATCC 19606 (+2 µg/ml RIF) MIC (µg/ml) |
|---|---|---|---|---|---|
| A | 0.25 | 2 | ≤0.06 | >64 | 0.125 |

P.A. = *Pseudomonas aeruginosa*
E.C. = *Eschehchia coli*
A.B. = *Acinetobacter baumannii*

Those skilled in the art will recognize, or be able to ascertain using no more than routine experimentation, many equivalents to the specific embodiments and methods described herein. Such equivalents are intended to be encompassed by the scope of the following claims.

The invention claimed is:

1. A crystalline form of the compound of Formula (A):

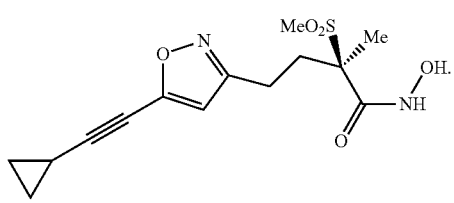

(A)

2. The crystalline form of claim 1 having low hygroscopicity.

3. The crystalline form of claim 1, which comprises rod-shaped crystals.

4. The crystalline form of claim 1, which exhibits an endotherm on differential scanning calorimetry between 75° C. and 90° C.

5. The crystalline form of claim 1, characterized by XRPD peaks at diffraction angles (2Theta) of 18.4 and 14.0 degrees.

6. The crystalline form of claim 5, further characterized by one or more additional XRPD peaks at diffraction angles (2Theta) of 3.9 and 2.5 and 4.4 degrees.

7. The crystalline form of claim 5, further characterized by one or more additional XRPD peaks at diffraction angles (2Theta) of 18.8 and/or 5.3 degrees and/or 21.8 degrees and/or 22.1 degrees and/or 18.0 degrees.

8. The crystalline form of claim 5, further characterized by additional XRPD peaks at diffraction angles (2Theta) of 18.8 and 5.3 degrees.

9. The crystalline form of claim 8, further characterized by additional XRPD peaks at diffraction angles (2Theta) of 21.8 degrees and 22.1 degrees.

10. A pharmaceutical composition, comprising:
an antibacterially effective amount of the crystalline form of claim 1,
and a pharmaceutically acceptable carrier.

11. A pharmaceutical combination, comprising:
an antibacterially effective amount of the crystalline form of claim 1,
an antibacterially effective amount of a second therapeutic agent, and
a pharmaceutically acceptable carrier.

12. The pharmaceutical combination of claim 11, wherein the second therapeutic agent is selected from the group consisting of Ampicillin, Piperacillin, Penicillin G, Ticarcillin, Imipenem, Meropenem, Azithromycin, Erythromycin, Aztreonam, Cefepime, Cefotaxime, Ceftriaxone, Ceftazidime, Ciprofloxacin, Levofloxacin, Clindamycin, Doxycycline, Gentamycin, Amikacin, Tobramycin, Tetracycline, Tigecycline, Rifampicin, Vancomycin and Polymyxin.

13. A method of making highly crystalline Compound (A) from non-crystalline Compound (A), which comprises dissolving non-crystalline Compound (A) in a halogenated organic solvent to form a solution, and contacting the solution with a hydrocarbon solvent to induce precipitation of crystalline Compound (A).

14. A crystalline form of the compound of Formula (A):

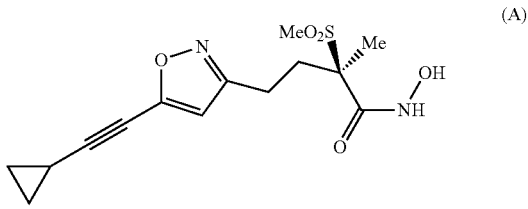 [SMILES: C[C@@](CCc1cc(C#CC2CC2)on1)(C(=O)NO)S(C)(=O)=O]

(A)

which is made by the method of claim 13.

15. A method for treating a subject with a Gram-negative bacterial infection, comprising:
administering to the subject in need thereof an antibacterially effective amount of the crystalline from of claimed 1.

* * * * *